(12) United States Patent  
Nakamoto et al.

(10) Patent No.: US 8,784,702 B2  
(45) Date of Patent: Jul. 22, 2014

(54) COPPER-CONTAINING NANOPARTICLES AND MANUFACTURING METHOD THEREFOR

(75) Inventors: Masami Nakamoto, Takarazuka (JP); Mari Yamamoto, Osaka (JP); Yukiyasu Kashiwagi, Kishiwada (JP); Yukio Yoshida, Osaka (JP); Hiroshi Kakiuchi, Osaka (JP); Shinsuke Matsumura, Osaka (JP)

(73) Assignees: Osaka Municipal Technical Research Institute, Osaka-Shi (JP); Daiken Chemical Co., Ltd., Osaka-Shi (JP)

( * ) Notice: Subject to any disclaimer, the term of this patent is extended or adjusted under 35 U.S.C. 154(b) by 489 days.

(21) Appl. No.: 13/058,681

(22) PCT Filed: Aug. 6, 2009

(86) PCT No.: PCT/JP2009/063962  
§ 371 (c)(1),  
(2), (4) Date: Apr. 28, 2011

(87) PCT Pub. No.: WO2010/018782  
PCT Pub. Date: Feb. 18, 2010

(65) Prior Publication Data  
US 2011/0193034 A1  Aug. 11, 2011

(30) Foreign Application Priority Data

Aug. 11, 2008 (JP) .................. 2008-207524

(51) Int. Cl.  
*H01B 1/02* (2006.01)  
*H01B 1/12* (2006.01)

(52) U.S. Cl.  
USPC ........ 252/519.21; 75/331; 420/501; 428/403; 428/570; 516/33; 977/773; 977/896

(58) Field of Classification Search  
USPC ........ 252/519.21; 75/331; 420/501; 428/403, 428/570; 516/33; 977/773, 896  
See application file for complete search history.

(56) References Cited

U.S. PATENT DOCUMENTS

| | | | |
|---|---|---|---|
| 6,262,129 B1 * | 7/2001 | Murray et al. | ............... 516/33 |
| 6,358,611 B1 | 3/2002 | Nagasawa et al. | |
| 2008/0087137 A1 * | 4/2008 | Shim et al. | ............... 75/331 |
| 2008/0138643 A1 | 6/2008 | Lee et al. | |
| 2008/0157029 A1 | 7/2008 | Lee et al. | |

FOREIGN PATENT DOCUMENTS

| | | | | |
|---|---|---|---|---|
| JP | 10-183207 A | | 7/1998 | |
| JP | 2004-273205 | * | 9/2004 | ............ H01B 1/22 |
| JP | 2004-273205 A | | 9/2004 | |
| JP | 2007-056321 A | | 3/2007 | |
| JP | 2007-63579 A | | 3/2007 | |
| JP | 2007-63580 A | | 3/2007 | |
| JP | 2008-19503 A | | 1/2008 | |
| JP | 2008-95195 A | | 6/2008 | |

* cited by examiner

*Primary Examiner* — Khanh Tuan Nguyen  
(74) *Attorney, Agent, or Firm* — Fox Rothschild LLP

(57) ABSTRACT

Copper-containing nanoparticles with excellent oxidation resistance is provided. The present invention relates to a method for manufacturing copper-containing nanoparticles including obtaining copper-containing nanoparticles that contain an organic component by heat treating an organic copper compound at a temperature equal to or higher than a decomposition initiation temperature of the compound and lower than a complete decomposition temperature of the compound in a non-oxidative atmosphere in the presence of an organic material containing a 1,2-alkanediol having 5 or more carbon atoms and/or a derivative thereof.

8 Claims, 19 Drawing Sheets

XRD OF CuNP/(IPx)₂Net 1,2-DDO IMMEDIATELY AFTER SYNTHESIS AND ONE MONTH LATER

CuNP/(C8)3N 1,2-DDO TG/DTA

TEM IMAGE OF CuNP/(C8)3N 1,2-DDO

PARTICLE SIZE DISTRIBUTION OF CuNP/(C8)3N 1,2-DDO

XRD OF CuNP/(C8)3N 1,2-DDO IMMEDIATELY AFTER SYNTHESIS

TEM IMAGE OF CuNP/1,2-DDO

PARTICLE SIZE DISTRIBUTION OF CuNP/1,2-DDO

XRD OF CuNP/1,2-DDO IMMEDIATELY AFTER SYNTHESIS

CuNP/(iPr)₂NEt 1,2-DDO TG/DTA

TEM IMAGE OF CuNP/(iPr)₂NEt 1,2-DDO

PARTICLE SIZE DISTRIBUTION OF CuNP/(iPr)₂NEt 1,2-DDO

XRD OF CuNP/(iPr)₃NEt 1,2-DDO IMMEDIATELY AFTER SYNTHESIS

CuNP/(2-EtC₆)₃N 1,2-DDO TG/DTA

TEM IMAGE OF CuNP/(2-EtC$_6$)$_3$N 1,2-DDO

PARTICLE SIZE DISTRIBUTION OF CuNP/(2-EtC$_6$)$_3$N 1,2-DDO

XRD OF CuNP/(2-EtC₆)₃N 1,2-DDO IMMEDIATELY AFTER SYNTHESIS

TG/DTA OF RAPID-SYNTHESIS CuNP/(2-EtC₆)₃N 1,2-DDO

TEM IMAGE OF RAPID-SYNTHESIS CuNP/(2-EtC$_6$)$_3$N 1,2-DDO

PARTICLE SIZE DISTRIBUTION OF RAPID-SYNTHESIS CuNP/(2-EtC$_6$)$_3$N 1,2-DDO

XRD IMMEDIATELY AFTER SYNTHESIS OF RAPID-SYNTHESIS CuNP/
(2-EtC₆)₃N 1,2-DDO

CuNP/(2-EtC$_6$)$_3$N 1-C$_{12}$OH TG/DTA

TEM IMAGE OF CuNP/(2-EtC$_6$)$_3$N 1-C$_{12}$OH

XRD OF CuNP/(2-EtC6)3N 1-C10OH IMMEDIATELY AFTER SYNTHESIS

XRD OF CuNP/(C8)3N 1,2-DDO IMMEDIATELY AFTER
SYNTHESIS AND ONE MONTH LATER

IMMEDIATELY AFTER SYNTHESIS    ONE MONTH LATER
CHANGES OVER TIME IN STRENGTH RATIO IN THE XRD PATTERN OF
CuNP/(C8)3N 1,2-DDO

XRD OF CuNP/(iPr)2NEt 1,2-DDO IMMEDIATELY AFTER SYNTHESIS
AND ONE MONTH LATER

XRD OF CuNP/(2-EtC$_6$)$_3$N 1,2-C$_{12}$(OH)$_2$ IMMEDIATELY AFTER SYNTHESIS AND ONE MONTH LATER

XRD OF RAPID-SYNTHESIS CuNP/(2-EtC$_6$)$_3$N 1,2-DDO IMMEDIATELY AFTER SYNTHESIS AND ONE MONTH AFTER SYNTHESIS

XRD OF CuNP/1,2-DDO IMMEDIATELY AFTER SYNTHESIS AND ONE MONTH LATER

STRENGTH RATIO IN THE XRD PATTERNS OF Cu AND $Cu_2O$ ACCORDING TO MEAN PARTICLE DIAMETER

COPPER-CONTAINING NANOPARTICLES AND MANUFACTURING METHOD THEREFOR

INCORPORATION BY REFERENCE

This application is a 371 of International Application No. PCT/JP2009/063962 filed Aug. 6, 2009, which claims priority to Japanese Patent Application No. 2008-207524 filed Aug. 11, 2008, the entire contents of which being hereby incorporated herein by reference.

TECHNICAL FIELD

The present invention relates to copper-containing nanoparticles, and to a manufacturing method therefor.

BACKGROUND ART

Metal nanoparticles are ultrafine particles 1 to 100 nm in diameter, which are known to fuse together spontaneously due to the extreme instability of the atoms on the particle surface, forming coarser particles. It is therefor normal to stabilize metal nanoparticles by covering the surfaces with organic protective groups. Unlike bulk metal, metal nanoparticles exhibit the characteristic properties of low melting point and low-temperature sintering, and are used in conductive pastes for forming wiring in engineering applications.

Metal nanoparticles are often classified according to the method of synthesis. Methods of metal nanoparticle synthesis are classified generally into two types: physical methods in which bulk metal is pulverized to obtain nanoparticles, and chemical methods in which zero-valent metal atoms are produced from a metal salt, metal complex or other precursor, and then aggregated to obtain nanoparticles. One physical method is pulverization, in which a ball mill or other device is used to grind metal down into smaller pieces, thereby obtaining metal nanoparticles. However, the particles obtained by this method have a broad particle size distribution, and it is difficult to obtain particles hundreds of nanometers or less in size. On the other hand, chemical methods include 1) the laser synthesis method, in which metal nanoparticles are synthesized by heating a reactive gas with a $CO_2$ laser, 2) the spray pyrolysis method, in which metal nanoparticles are obtained by spraying a metal salt solution in a high-temperature atmosphere, causing the instantaneous evaporation and pyrolysis of the solution, and 3) the reduction method, in which metal nanoparticles are obtained by a reduction reaction from a metal salt solution, but none of these methods are suited to quantity synthesis.

To resolve these problems of existing metal nanoparticle synthesis methods, the inventors in this case developed a thermal decomposition control method whereby a metal nanoparticle can be synthesized simply by heating a metal complex as the metal source in the absence of a solvent (Patent Document 1, Patent Document 2, etc.). The primary feature of this thermal decomposition control method is the simplicity of heating in the absence of a solvent, which allows for quantity synthesis. It has also been found that adding an organic compound or the like with a mild reducing character to the reaction system serves to moderate the reaction conditions, and design of the particle diameter, shape and surface protective layer is also possible.

Metal nanoparticles are being actively studied for industrial application in a variety of fields, including microwiring technologies using metal nanoparticles. Because the surfaces of metal nanoparticles are covered with an organic protective layer, they are highly solvent-dispersible, and wiring at lower temperatures than before is anticipated using the characteristic low-temperature fusion property of nanoparticles. At present, most applications involve wiring materials using silver nanoparticles, but silver is rare and therefore expensive, and it is also considered problematic because when used under conditions of high humidity it is extremely liable to a phenomenon called migration, in which the silver ionizes and is re-deposited outside the circuits, causing short-circuits between electrodes. Attention is therefore shifting to copper nanoparticles, which are expected to be cheaper and to cause little or no migration.

The problem with copper is that it readily oxidizes in air. In fact, synthesis of copper particles has already been studied by a variety of methods (Patent Document 3, Patent Document 4, etc.), but no technique has focused on the problem of oxidation, and no technology has been proposed for solving the problem of oxidation.

Patent Document 1: Japanese Patent Application Publication No. 2007-63579
Patent Document 2: Japanese Patent Application Publication No. 2007-63580
Patent Document 3: Japanese Patent Application Publication No. 2008-19503
Patent Document 4: Japanese Patent Application Publication No. 2008-95195

DISCLOSURE OF THE INVENTION

It is therefore an object of the present invention to provide copper-containing nanoparticles having excellent oxidation resistance.

In light of the problems of prior art, the inventors in this case discovered as a result of exhaustive research that the aforementioned object can be achieved by means of a particle obtained under specific conditions, and perfected the present invention.

That is, the present invent relates to the following copper nanoparticle, and to a manufacturing method therefor.

1. A method for manufacturing copper-containing nanoparticles, comprising a step of obtaining copper-containing nanoparticles that contain an organic component by heat treating an organic copper compound at a temperature equal to or higher than a decomposition initiation temperature of the compound and lower than a complete decomposition temperature of the compound in a non-oxidative atmosphere in the presence of an organic material containing a 1,2-alkanediol having 5 or more carbon atoms and/or a derivative thereof.

2. The manufacturing method according to 1 above, wherein the number of carbon atoms in the 1,2-alkanediol or a derivative thereof is 8 to 30.

3. The manufacturing method according to 1 above, wherein the organic material further contains a tertiary amine compound.

4. The manufacturing method according to 1 above, wherein the organic copper compound is a copper salt of an organic acid having 5 or more carbon atoms.

5. The manufacturing method according to 1 above, wherein heat treatment is performed under conditions with no primary amine or secondary amine present.

6. Copper-containing nanoparticles comprising an organic component and $Cu_2O$, wherein an intensity ratio of $Cu_2O$ in an X-ray diffraction pattern is 50% or less given 100% as the total of intensities of $Cu$ and $Cu_2O$.

7. The copper-containing nanoparticles according to 6 above, wherein the organic component contains at least one of a 1,2-alkanediol with 5 or more carbon atoms, a derivative thereof and a component derived from these.

8. The copper-containing nanoparticles according to 6 above, wherein the content of the organic component is 25 wt % or less.

9. The copper-containing nanoparticles according to 6 above, wherein the change in the intensities of the Cu and $Cu_2O$ in the X-ray diffraction pattern immediately after oxidation resistance testing in which the copper-containing nanoparticles immediately after synthesis is left for 1 month at a temperature of 25° C. and a humidity of 60% in air is no more than 3% of the intensities of the Cu and $Cu_2O$ in the X-ray diffraction pattern of the copper-containing nanoparticles immediately after synthesis.

10. The copper-containing nanoparticles according to 6 above, which is obtained by the manufacturing method according to 1 above.

11. The copper-containing nanoparticles according to 6 above, which is used for wiring formation purposes.

12. The copper-containing nanoparticles according to 6 above, which is used for bonding purposes.

13. A paste comprising the copper-containing nanoparticles according to 6 above, a solvent and at least one type of viscosity modifying resin.

14. A method for forming an electrical junction or electrical circuit, comprising a step of forming an electrical junction region or pattern using copper-containing nanoparticles according to 6 above, or a paste containing that particle, and a step of baking the electrical junction region or pattern, in a reducing atmosphere at 400° C. or less to obtain an electrical junction or electrical circuit consisting of a baked material.

ADVANTAGES OF THE INVENTION

In the manufacturing method of the present invention, copper-containing nanoparticles can be manufactured efficiently by heat treating a specific organic copper compound under the specific conditions. In particular, it is possible to manufacturing copper-containing nanoparticles comprising cuprous oxide ($Cu_2O$).

Because the copper-containing nanoparticles of the present invention contains an organic component and cuprous oxide, it has excellent dispersion stability, and can also provide excellent oxidation resistance. Because of this excellent dispersion stability, a solubilized state can be obtained by dispersing the copper-containing nanoparticles in a solvent. For example, it can be used as is dispersed in toluene, hexane, undecane or the like, and can also be mixed with a known paste-forming agent and used as a paste. Since it also has excellent oxidation resistance, it maintains the same quality even when stored for a long period of time.

The nanoparticles of the present invention having such features can provide a variety of properties (such as catalytic activity, conductivity, ultraviolet shielding, heat ray shielding, antibacterial properties, antifouling properties, rust resistance, corrosion resistance and the like). It can therefore be used favorably for a wide variety of applications, such as electronic materials (printed wiring, conductive materials, optical elements and the like), magnetic materials (magnetic recording media, electromagnetic wave absorbers, electromagnetic resonators and the like), catalytic materials (high-speed reaction catalysts, sensors and the like), structural materials (far infrared materials, composite coat-forming materials and the like), ceramic and metal materials (sintering aids, coating materials and the like), medical materials and the like for example. In particular, the copper-containing nanoparticles of the present invention car be used favorably for wiring formation and bonding purposes (substrate interlayer connections).

BEST MODE FOR CARRYING OUT THE INVENTION

1. Copper-Containing Nanoparticles Manufacturing Method

Figure 1:
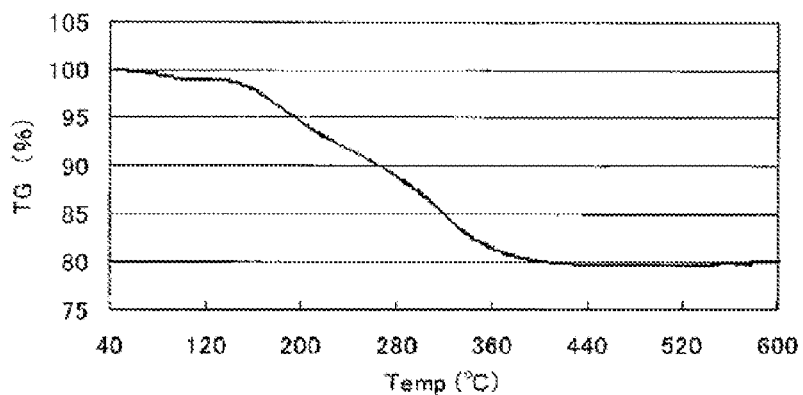
FIG. 1 shows the results for thermogravimetric (TG) change in TG/DTA measurement of the powder obtained in Example 1.

In the copper-containing nanoparticles manufacturing method of the present invention, copper-containing nanoparticles comprising an organic component is obtained by heat treating an organic copper compound at a temperature not less than the decomposition initiation temperature of the compound but lower than the complete decomposition temperature of the compound in a non-oxidative atmosphere in the presence of an organic material comprising a 1,2-alkanediol having 5 or more carbon atoms and/or a derivative thereof.

In the present invention, an organic copper compound may be a copper salt of an organic acid, a copper alkoxide, a copper acetylacetonate or the like. One or two or more of these can be used, but from the standpoint of controlling the heat treatment temperature it is desirable to use one organic copper compound.

In particular, a copper salt of an organic acid can be used favorably in the present invention. Examples of such copper salts include salts of stearic acid, naphthenic acid, octylic acid, octanic acid, benzoic acid, n-decanoic acid, paratoluic acid, butyric acid, caproic acid, palmitic acid, oleic acid, myristic acid, lauric acid, linoleic acid, linolenic acid, ricinoleic acid and other monocarboxylic acid salts as well as salts of malonic acid, succinic acid, maleic acid, fumaric acid, isophthalic acid, terephthalic acid, glutaric acid, adipic acid, tartaric acid, citric acid, pyruvic acid and other dicarboxylic acids and the like. Of these, it is more desirable to use a copper salt of an organic acid with 5 or more carbon atoms (especially 6 or more carbon atoms, particularly 8 to 14 carbon atoms).

A 1,2-alkanediol with 5 or more carbon atoms and/or a derivative thereof (hereunder sometimes called "the diol of the present invention") is used as an organic material. The number of carbon atoms is preferably at least 6, or more preferably at least 10, or still more preferably 12 to 30. Examples of such 1,2-alkanediols include 1,2-hexanediol, 1,2-octanediol, 1,2-nonanediol, 1,2-decanediol, 1,2-undecanediol, 1,2-dodecanediol, 1,2-tridecanediol and the like for example. The 1,2-alkanediol is preferably a straight-chain alkanediol. Examples of the aforementioned derivatives include those in which a hydrogen atom bonded to carbon atom of ethylene glycol is replaced with another substituent. Examples of the substituent in this case include amino, halogen, nitro, nitroso, mercapto, sulfo, sulfino, methoxy, ethoxy, cyano, carboxyl, carbonyl, phenyl, phenoxy, benzoyl and acetyl groups and the like for example. In the case of the aforementioned derivative, the number of carbon atoms includes the number of carbon atoms in the substituent.

The amount of the diol used in the present invention is not limited, but is normally about 100 to 300 moles or especially 150 to 250 moles per 100 moles of the organic copper compound.

A tertiary amine compound can also be used as necessary as an organic material in the present invention. A tertiary amine compound having the general formula $R^1R^2R^3$ (wherein $R^1$ to $R^3$ independently represent an alkyl group or aryl group that may have a substituent, and $R^1$ to $R^3$ may be linked together to form a cyclic structure) can be used. Examples of substituents include amino, halogen, nitro, nitroso, mercapto, sulfo, sulfino, methoxy, ethoxy, cyano, carboxyl, carbonyl, phenyl, phenoxy, benzol and acetyl groups and the like for example. The number of carbon atoms in the aforementioned alkyl or aryl groups (including the number of carbon atoms in the substituents when such are present) is normally about 1 to 12 or especially 3 to 12 in the case of an alkyl group and normally about 6 to 18 or especially 6 to 12 in the case of an aryl group. Specific examples of preferred tertiary amine compounds include tributylamine, trioctylamine, triisobutylamine and N,N-diisopropylethylamine as well as tris(2-ethylhexyl)amine and the like. One or two or more of these can be used.

The amount of the tertiary amine compound used can be set appropriately according to the type of tertiary amine compound and the like, but is normally about 100 to 300 moles or especially 150 to 250 moles per 100 males of the organic copper compound.

In the manufacturing method of the present invention, an amine (primary or secondary amine) other than a tertiary amine can be included as long as it does not detract from the effects of the present invention, but it is especially desirable to perform heat treatment under conditions with no primary or secondary amine present. This allows copper-containing nanoparticles with the desired oxidation resistance to be obtained more reliably.

In the present invention, heat treatment is performed in a non-oxidative atmosphere at a temperature equal to or higher than the decomposition initiation temperature and lower than the complete decomposition temperature of the organic copper compound. Copper-containing nanoparticles containing an organic component is obtained in this way.

The heat treatment atmosphere it not limited as long as it is non-oxidative, and may be an inactive gas, a reducing atmosphere or the like. In the present invention, it is especially desirable to perform heat treatment in inactive gas. Nitrogen, carbon dioxide, argon, helium or the like can be use as the inactive gas.

The heat treatment temperature is a temperature equal to or higher than the decomposition initiation temperature and lower than the complete decomposition temperature of the organic copper compound. The decomposition initiation temperature is the temperature at which the organic copper compound breaks down and the organic component begins to evaporate in TG/DTA measurement, while the complete decomposition temperature is the temperature at which the organic component of the organic copper compound is completely evaporated. In the present invention, the temperature can be set appropriately within this range according to the type of organic copper compound and the like. For example, when using an organic copper compound with a decomposition initiation temperature of about 100° C. and a complete decomposition temperature of about 400° C., the heat treatment temperature can be maintained within the temperature range of 100 to 400° C. Heat treatment can also be performed favorably within a temperature range of 100 to 300° C. (especially 100 to 200° C.) for example as described in the examples below.

As mentioned above, it is desirable to use one type of organic copper compound from the standpoint of controlling the heat treatment temperature, but when using two or more organic copper compounds, the heat treatment temperature can be set based on the compound having the highest decomposition initiation temperature.

The heat treatment temperature holding time can be changed appropriately according to the kind of organic copper compound used, the heat treatment temperature and the like.

After completion of heat treatment, the compound is cooled to room temperature and purified as necessary. Purification can be accomplished by a well-known purification method, such as centrifugation, membrane purification, solvent extraction or the like.

Copper-containing nanoparticles comprising an organic component can be obtained by the manufacturing method of the present invention. As well as a nanoparticle composed substantially of an organic component and copper, it is possible to obtain a nanoparticle composed effectively of an organic component, copper and cuprous oxide. In the manufacturing method of the present invention, the particle size and/or $Cu_2O$ content can be controlled more easily and reliably by changing the type of tertiary amine in particular. In particular, the particle size and/or $Cu_2O$ content can be controlled more easily and reliably by changing either the molecular size of the tertiary amine, the level of steric hindrance or both.

2. Copper-Containing Nanoparticles

The copper-containing nanoparticles of the present invention is copper-containing nanoparticles comprising an organic component and $Cu_2O$, wherein the intensity ratio of $Cu_2O$ given 100% as the total intensity of the Cu and $Cu_2O$ in the X-ray diffraction pattern is 50% or less.

The copper-containing nanoparticles of the present invention comprises an organic component and $Cu_2O$. The copper-containing nanoparticles of the present invention is preferably obtained by the aforementioned manufacturing method of the present invention. That is, it is preferably copper-containing nanoparticles obtained by copper-containing nanoparticles manufacturing method wherein an organic copper compound is heat treated at a temperature equal to or higher than the decomposition initiation temperature of the compound and lower than the complete decomposition temperature of the compound in a non-oxidative atmosphere in the presence of an organic material comprising a 1,2-alkanediol having 5 or more carbon atoms and/or a derivative thereof, thereby obtaining copper-containing nanoparticles that contains an organic component.

The organic component is not particularly limited, but since the copper-containing nanoparticles of the present invention is preferably obtained by the manufacturing method of the present invention, the organic component preferably includes at least one of a 1,2-alkanediol with 5 or more carbon atoms, a derivative thereof and a component derived from these as an organic component. The aforementioned derived component is preferably an organic component produced by subjecting a 1,2-alkanediol with 5 or more carbon atoms and/or a derivative thereof to the aforementioned heat treatment.

The content of the organic component is normally 25 wt % or less, or especially 20 wt % or less. The minimum value of the content of the organic component is not particularly limited but is normally about 1 wt %.

In terms of the content of $Cu_2O$ (cuprous oxide), the intensity ratio of $Cu_2O$ is 50% or less (especially 10% or less) given 100% as the total intensity of Cu and $Cu_2O$ in the X-ray diffraction pattern. The minimum value of the intensity ratio is not particularly limited, but can normally be about 0.1%. Thus, excellent oxidation resistance can be obtained in the present invention by deliberately including $Cu_2O$ in the copper-containing nanoparticles, but in a relatively small amount. More specifically, the change in the intensities of the Cu and $Cu_2O$ in the X-ray diffraction pattern immediately after oxidation resistance testing in which the copper-containing nanoparticles immediately after synthesis is left for 1 month at a temperature of 25° C. and a humidity of 60% in air is no more than 3% (preferably no more than 2%) of the intensities of the Cu and $Cu_2O$ in the X-ray diffraction pattern of the copper-containing nanoparticles immediately after synthesis.

The mean particle diameter of the copper-containing nanoparticles of the present invention is not particularly limited, but is usually about 3 to 500 nm or preferably 7 to 50 nm. In particular, the copper-containing nanoparticles having an mean particle diameter of 80 nm or less can be provide by the present invention, something that has been difficult to obtain with prior art. In the manufacturing method of the present invention, the mean particle diameter can be controlled easily and reliably by changing the manufacturing conditions (especially the type of tertiary amine and/or 1,2-alkanediol).

Because the copper-containing nanoparticles of the present invention has excellent dispersion stability, a solubilized state can be obtained by dispersing it in a solvent for example. It can thus be used favorably in the form of a paste containing the copper-containing nanoparticles and at least one of a solvent and a viscosity modifying resin. The solvent is not particularly limited, and examples include terpene solvents, ketone solvents, alcohol solvents, ester solvents, ether solvents, aliphatic hydrocarbon solvents, aromatic hydrocarbon solvents, cellosolve solvents, carbitol solvents and the like. More specific examples include terpineol, methylethyl ketone, acetone, isopropanol, butyl carbitol, decane, undecane, tetradecane, benzene, toluene, hexane, diethyl ether, kerosene and other organic solvents. The viscosity modifying resin is not particularly limited, and phenol resins, melamine resins, alkyd resins and other thermosetting resins, phenoxy resins, acrylic resins and other thermoplastic resins, and epoxy resins and other curing agent-cured resins can be used for example. In the case of a paste, the content of the copper-containing nanoparticles can be set appropriately within the range of 20 to 90 wt %.

The present invention also encompasses a method for forming an electrical junction or electrical circuit, comprising 1) a step of forming an electrical junction region or pattern with the copper-containing nanoparticles of the present invention or a paste containing the same, and 2) a step of baking the electrical junction region or pattern at 400° C. or less in a reducing atmosphere to obtain an electrical junction or electrical circuit.

The electrical junction region can be formed by methods similar to the soldering used to bond two circuits for example. Known methods used for circuit formation, electrode formation or the like can be used for the step of forming the pattern. For example, a specific circuit pattern, electrode pattern or the like can be formed by a printing method such as screen printing, inkjet printing or the like.

Next, the electrical junction region or pattern is baked in a reducing atmosphere. It is thus possible to obtain an electrical junction or electrical circuit formed from a baked body. The baking temperature can be set appropriately according to the type of copper-containing nanoparticles, the paste composition and the like, but is normally 400° C. or less, or preferably 150 to 400° C., or more preferably 180 to 380° C., or most preferably 280 to 380° C. The reducing atmosphere can be an atmosphere containing reducing gas. For example, a mixed gas atmosphere containing 1 to 10 vol % hydrogen gas, with the remainder being inactive gas, can be adopted by preference. Argon gas, helium gas or the like or nitrogen gas can be used as the inactive gas. The baking time can be set appropriately according to the baking temperature and the like, but is normally about 1 to 10 hours.

Baking in atmosphere or in an oxidizing atmosphere can be performed before baking in the aforementioned reducing atmosphere if necessary. In this case, the baking temperature is normally 150 to 400° C. or preferably 280 to 380° C. This baking serves to control pore production, thereby further increasing the density of the baked film and improving its electrical characterstics.

Thus, in the present invention a highly conductive electrical junction region or pattern (electrode pattern, circuit pattern or wiring pattern) can be provided using the nanoparticle of the present invention or a paste containing the same, and baking (heat treating) it in a reducing atmosphere. The electrical junction region or pattern is normally in the form of a film, the thickness of which is normally 1 to 50 µm or preferably 1 to 10 µm.

EXAMPLES

The features of the present invention are explained in more detail below using examples and comparative examples. However, the scope of the present invention is not limited by the examples.

(1) Reagents and Measurement Equipment

Reagents used in synthesis and measurement: Tributylamine, trioctylamine, triisobutylamine, N,N-diisopropylethylamine, tris(2-ethylhexyl)amine, 1,2-dodecanediol, 1,2-octanediol, 1-dodecanol and diethyl tartrate were purchased from Nacalai Tesque Inc., copper octoate from Mitsuwa Chemical Co., and 3-octadecyloxy-1,2-propanediol from Tokyo Chemical Industry Co.

Didodecyl tartrate was prepared by an ester exchange reaction of diethyl tartrate and 1-dodecanol.

TG/DTA: measured at a program rate of 10° C./minute in a nitrogen atmosphere using a Seico Electronics SSC/5200 Thermal Analyzer.

Powder X-ray diffractometer (XRD): Rigaku RINT2500.

Transmission electron microscope (TEM): A JEOL JEM2100 was used. The observation samples were prepared by adding toluene to copper-containing nanoparticles, dispersing them by exposure to ultrasound, and dripping and drying the resulting liquid on a cooper grid with a carbon support film.

(2) Chemical Notation

In these examples, the compounds are abbreviated as follows.

Copper octoate: $(C_7COO)_2Cu$
Tributylamine: $(C_4)_3N$
Trioctylamine: $(C_8)_3N$
Triisobutylamine: $(iBu)_3N$
N,N-diisopropylethylamine: $(iPr)_2NEt$
Tris(2-ethylhexyl)amine: $(2-EtC_6)_3N$
1,2-octanediol: 1,2-ODO
1,2-dodecanediol: 1,2-DDO
1-dodecanol: $1-C_{12}OH$
3-octanedecyloxy-1,2-propanediol: 3-ODO-1,2-PDO
Didodecyl tartrate: DDT Copper-containing nanoparticles synthesized from $(C_2COO)_2Cu$, $(C_8)_3N$ and 1,2-DDO is represented as CuNP/$(C_8)_3N$ 1,2-DDO.

(3) Methods for Measuring Physical Properties

Mean particle diameter: this was measured with the aforementioned transmission electrons microscope, and the arithmetic average of the diameters of 300 randomly selected particles was calculated and given as the mean particle diameter.

Content of metal component: this was determined from thermogravimetric (TG) changes in TG/DTA measurement using the aforementioned thermal analyzer.

Oxidation resistance test: A glass slide was used to press copper-containing nanoparticle powder into a 1.7 cm high×2 cm wide×0.3 mm deep indentation in a glass plate for powder X-ray diffraction measurement. This sample was first measured with an X-ray diffractometer and then left as is for 1 month at a temperature of 25° C. and a humidity of 60% in atmosphere, and the same sample was then measured again with an X-ray diffractometer and the change in the intensities of the Cu and $Cu_2O$ in the X-ray diffraction pattern was determined.

Example 1

Figure 2:
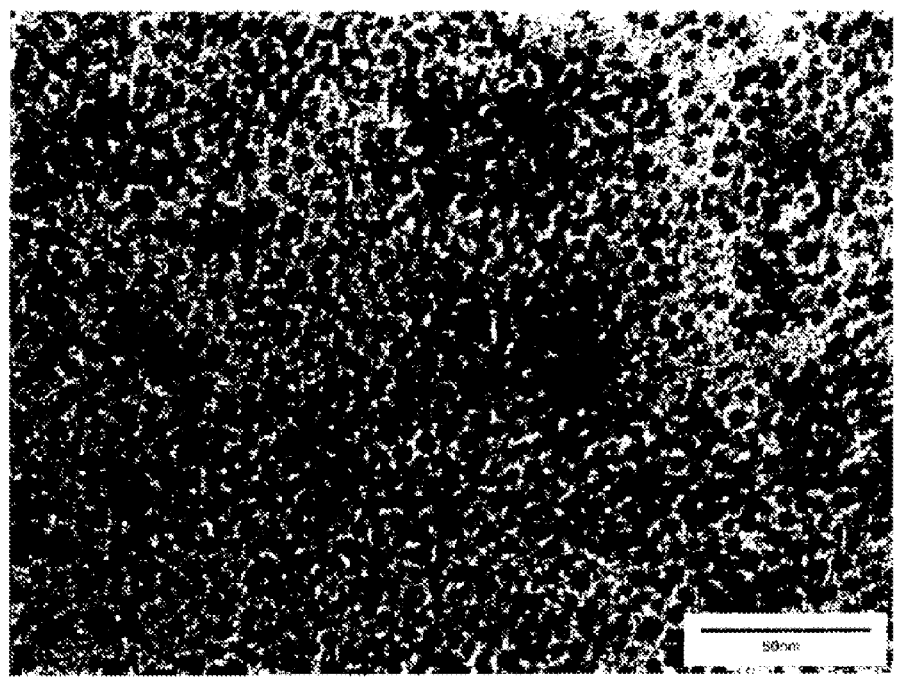
FIG. 2 shows a TEM image of the powder obtained in Example 1.
Figure 3:
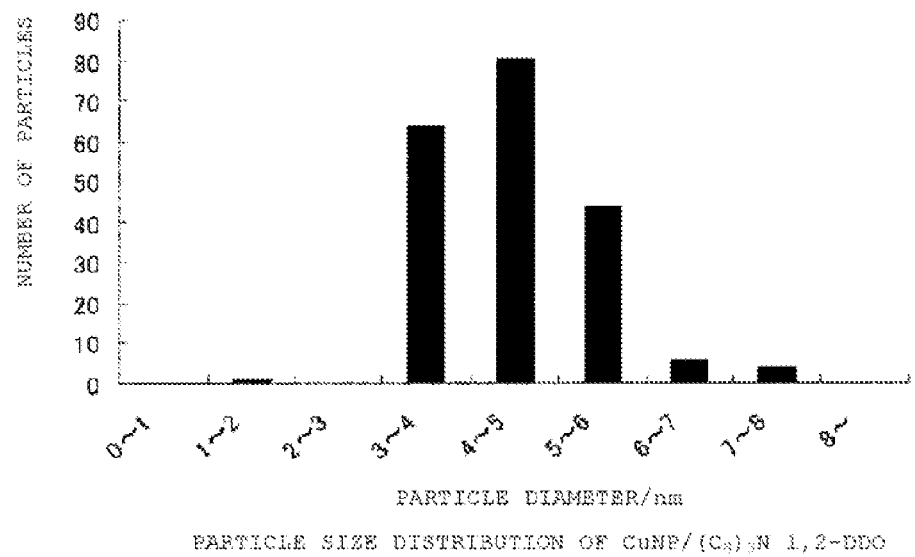
FIG. 3 shows the particle size distribution of the powder obtained in Example 1.
Figure 4:
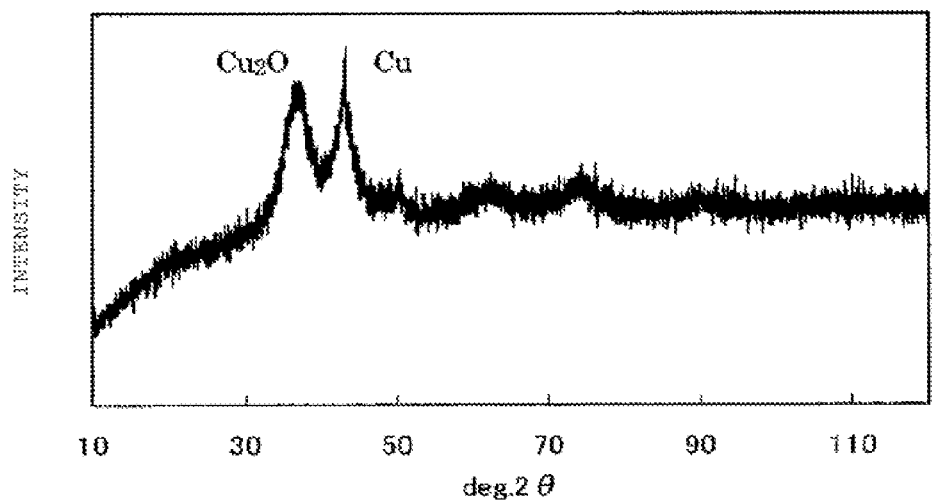
FIG. 4 shows the results of X-ray diffraction analysis (XRD) of the powder obtained in Example 1.

Synthesis of CuNP/$(C_8)_3N$ 1,2-DDO $(C_2COO)_2Cu$ (1.75 g, 5.0 mmol) was added to 1,2-DOC (2.02 g, 10 mmol) and $(C_8)_3N$ (3.57 g, 10 mmol), and the mixture was maintained for 16 hours at 160° C. in a nitrogen atmosphere and then cooled to room temperature. This was washed with acetone (20 ml), filtered with a Kiriyama funnel, and dried under reduced pressure to obtain a blackish-brown powder (yield 0.38 g/95%, metal content 80%, mean particle diameter 4.5±0.93 nm). FIG. 1 shows the results for thermogravimetric (TG) change according to TG/DTA measurement, FIG. 2 shows a TEM image, FIG. 3 shows the particle size distribution, and FIG. 4 shows the results of X-ray diffraction analysis (XRD) of the resulting powder.

Example 2

Figure 5:
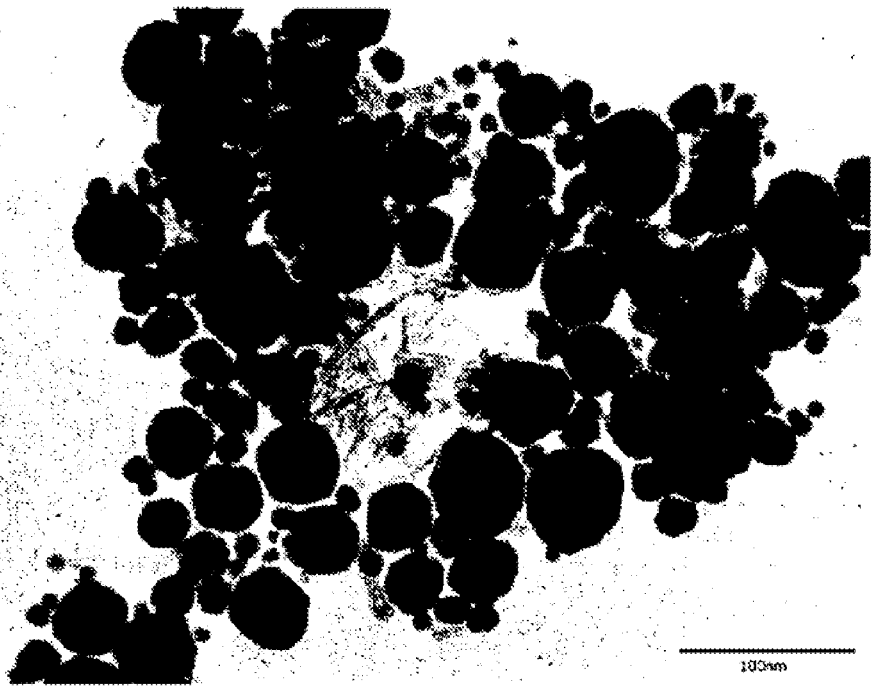
FIG. 5 shows a TEM image of the powder obtained in Example 2.
Figure 6:
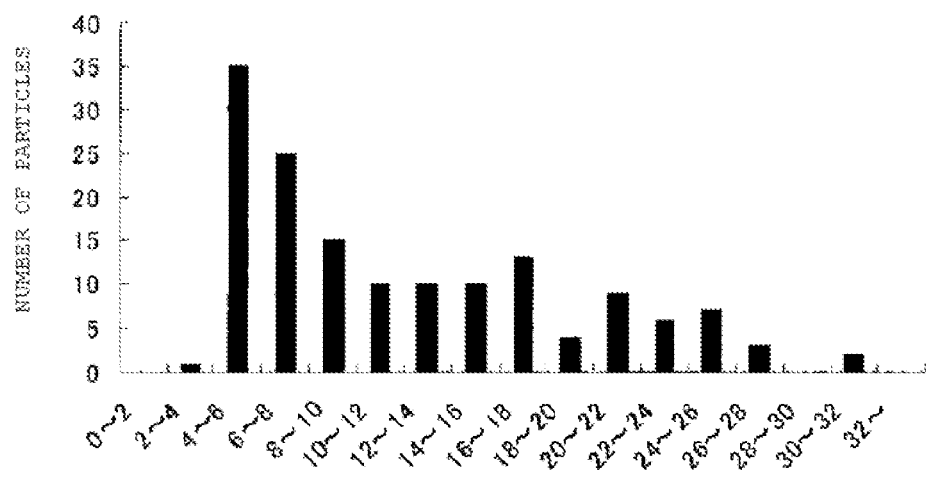
FIG. 6 shows the particle size distribution of the powder obtained in Example 2.
Figure 7:
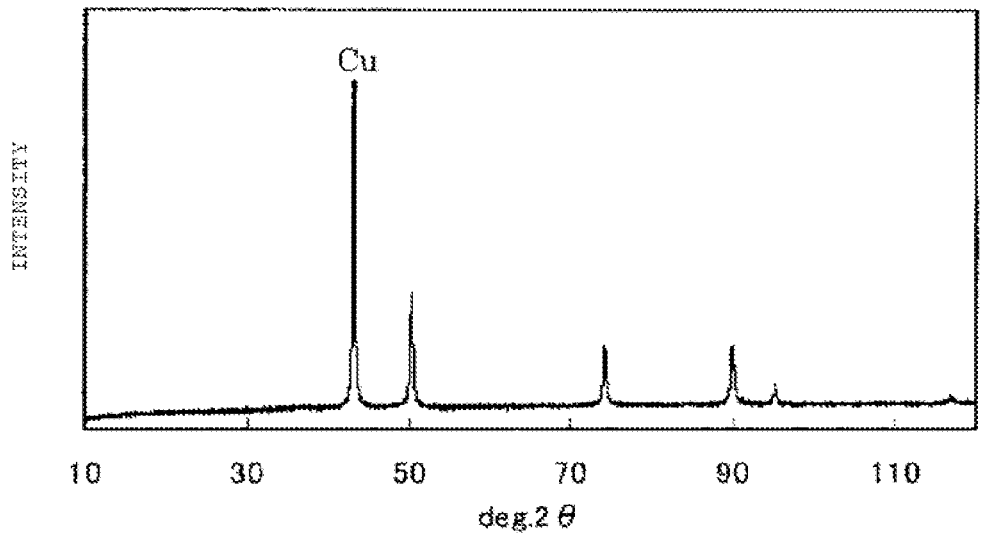
FIG. 7 shows the results of X-ray diffraction analysis (XRD) of the powder obtained in Example 2.

Synthesis of CuNP/1,2-DDO $(C_2COO)_2Cu$ (1.75 g, 5.0 mmol) was added to 1,2-DDO (2.02 g, 10 mmol), and the mixture was maintained for 16 hours at 160° C. in a nitrogen atmosphere and then cooled to room temperature. This was washed with acetone (20 ml), filtered with a Kiriyama funnel, and dried under reduced pressure to obtain a blackish-brown powder (yield 0.24 g/76%, metal content 99.8%, mean particle diameter 24.2±13.9 nm). FIG. 5 shows a TEM image, FIG. 6 shows the particle size distribution, and FIG. 7 shows the results of X-ray diffraction analysis (XRD) of the resulting powder.

Example 3

Synthesis of CuNP/(iPr)$_2$NEt 1,2-DDO

Figure 8:
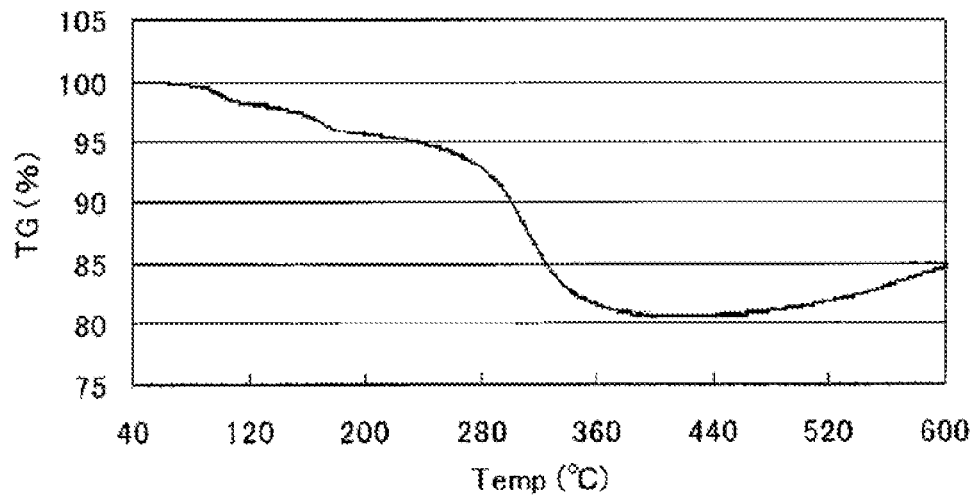
FIG. 8 shows the results for thermogravimetric (TG) change in TG/DTA measurement of the powder obtained in Example 3.
Figure 9:
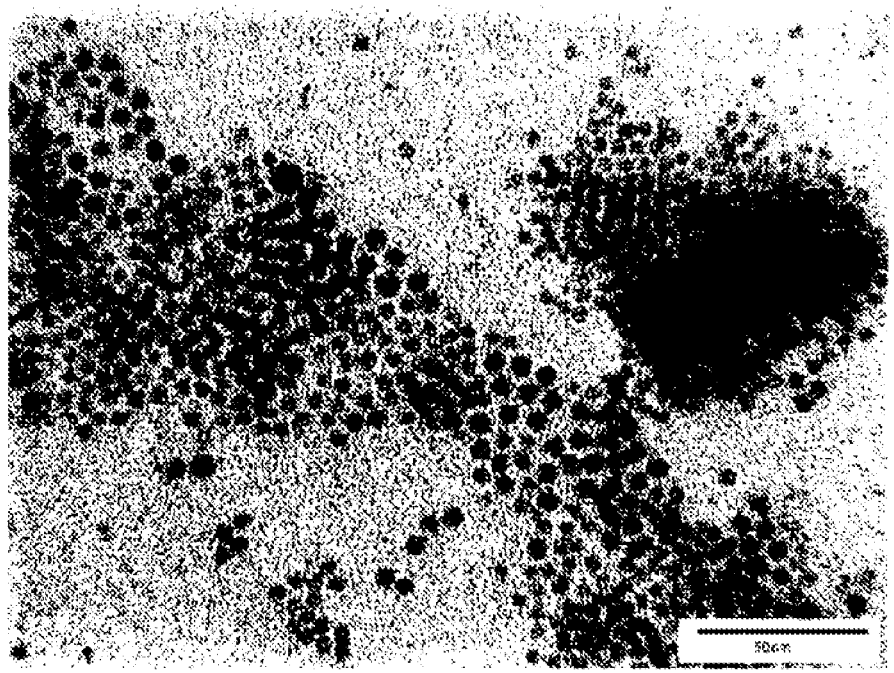
FIG. 9 shows a TEM image of the powder obtained in Example 3.
Figure 10:
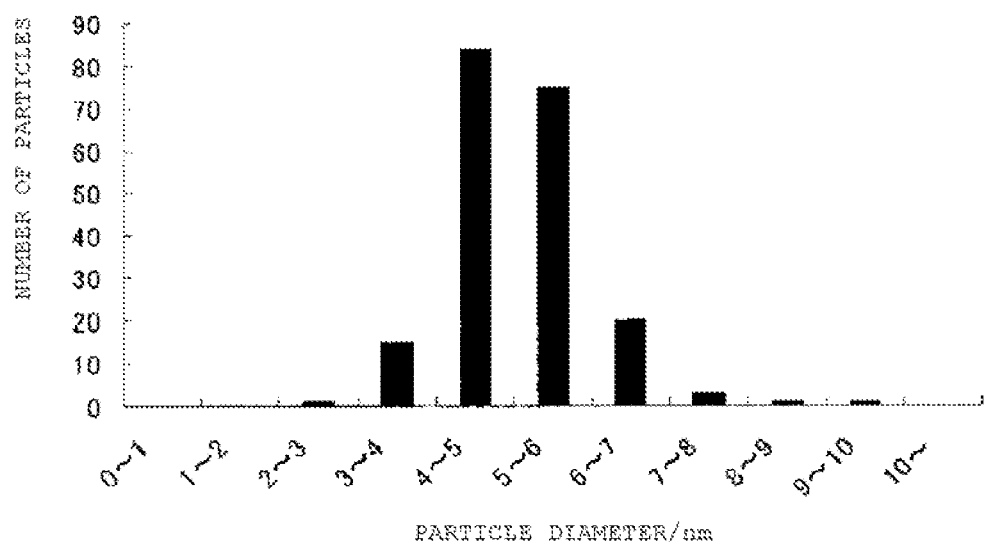
FIG. 10 shows the particle size distribution of the powder obtained in Example 3.
Figure 11:
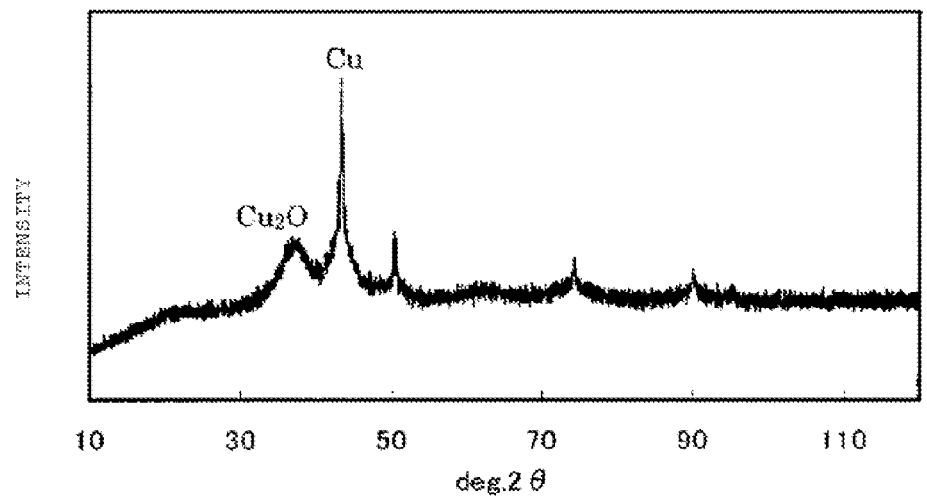
FIG. 11 shows the results of X-ray diffraction analysis (XRD) of the powder obtained in Example 3.

A powder (yield 0.31 g/79%, metal content 81%, mean particle diameter 5.1±0.90 nm) was obtained by a reaction similar to that of Example 1 except that (iPr)$_2$NEt was substituted for the amine (C$_8$)$_3$N used in Example 1. FIG. 8 shows the results for thermogravimetric (TG) change according to TG/TA measurement, FIG. 9 shows a TEM image, FIG. 10 shows the particle size distribution, and FIG. 11 shows the results of X-ray diffraction analysis (XRD) of the resulting powder.

Example 4

Synthesis of CuNP/(2-EtC$_6$)$_3$N 1,2-DDO

Figure 12:
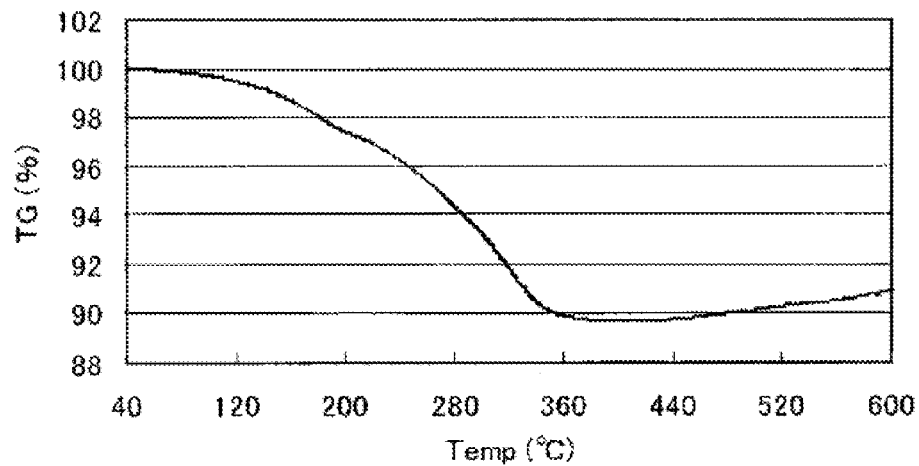
FIG. 12 shows the results for thermogravimetric (TG) change in TG/DTA measurement of the powder obtained in Example 4.
Figure 13:
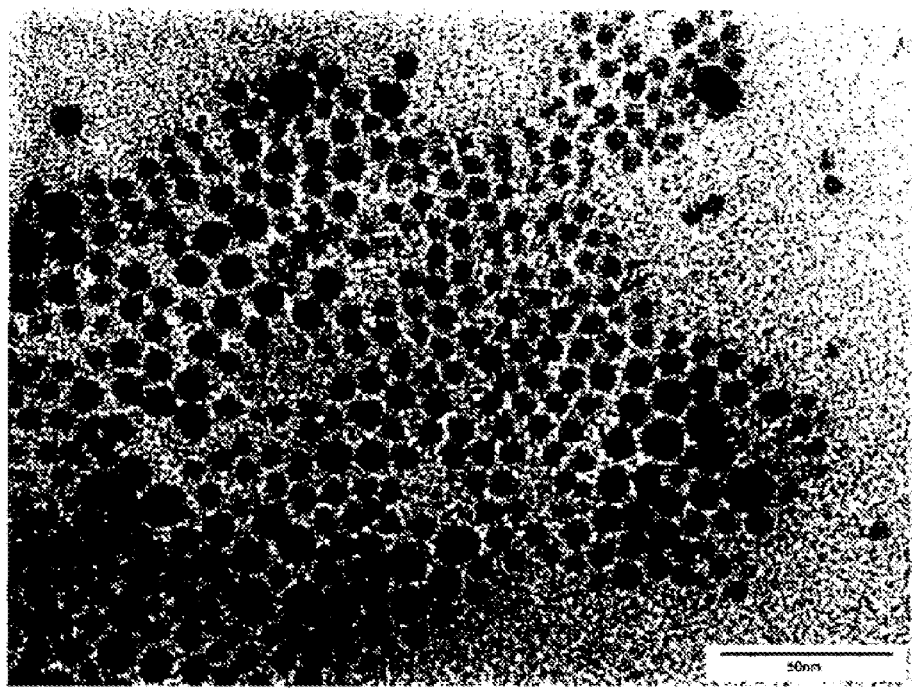
FIG. 13 shows a TEM image of the powder obtained in Example 4.
Figure 14:
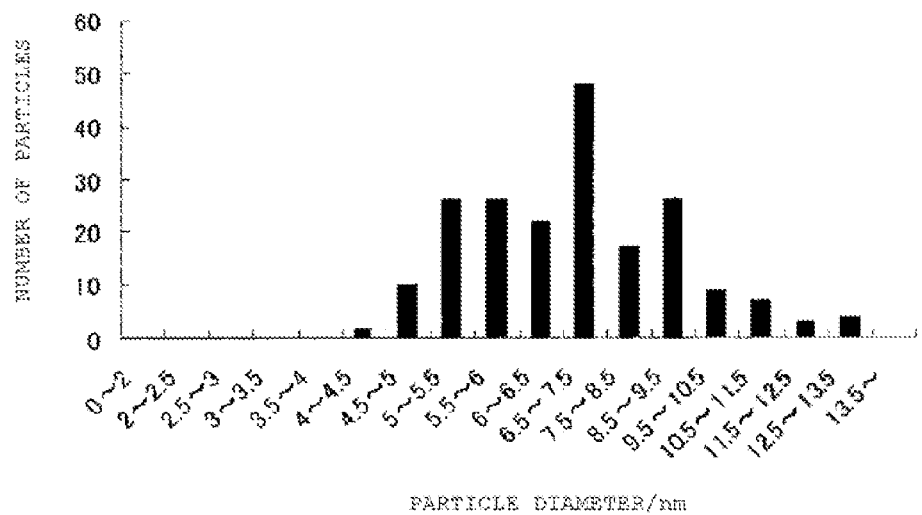
FIG. 14 shows the particle size distribution of the powder obtained in Example 4.
Figure 15:
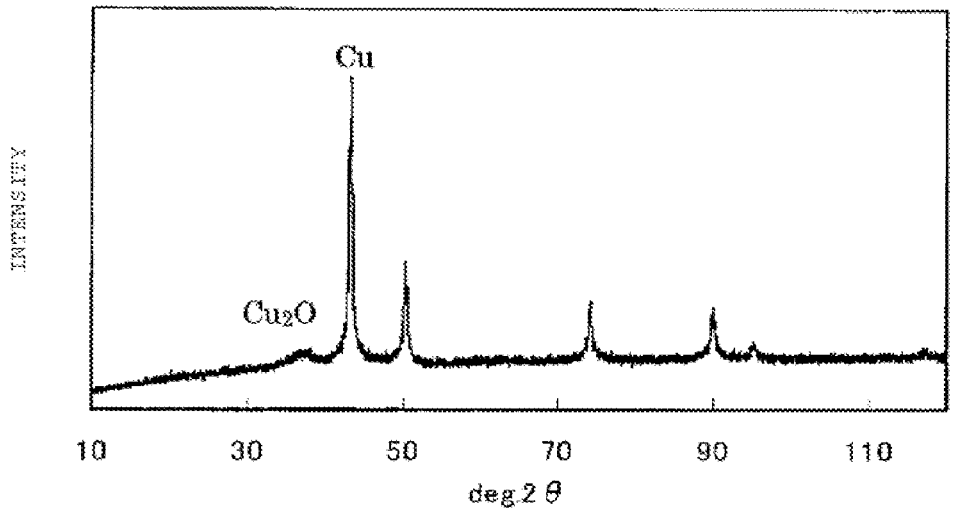
FIG. 15 shows the results of X-ray diffraction analysis (XRD) of the powder obtained in Example 4.

A powder (yield 0.30 g/87%, metal content 90%, mean particle diameter (7.2±1.9 nm) was obtained by a reaction similar to that of Example 1 except that (2-EtC$_6$)$_3$N was substituted for the amine (C$_8$)$_3$N used in Example 1. FIG. 12 shows the results for thermogravimetric (TG) change according to TG/DTA measurement, FIG. 13 shows a TEM image, FIG. 14 shows the particle size distribution, and FIG. 15 shows the results of X-ray diffraction analysis (XRD) of the resulting powder.

Example 5

High-Temperature Rapid Synthesis of CuNP/(2-EtC$_6$)$_3$N 1,2-DDO

Figure 16:
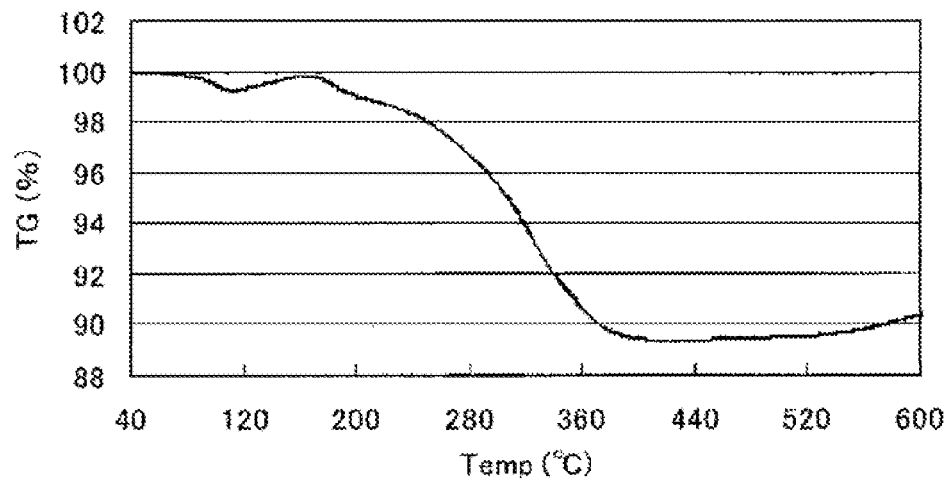
FIG. 16 shows the results for thermogravimetric (TG) change in TG/DTA measurement of the powder obtained in Example 5.
Figure 17:
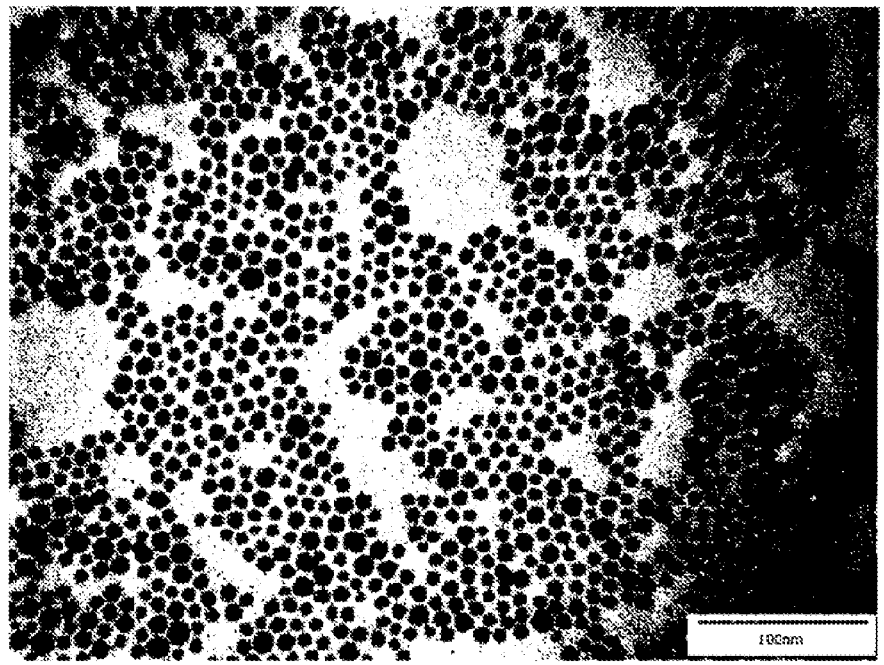
FIG. 17 shows a TEM image of the powder obtained in Example 5.
Figure 18:
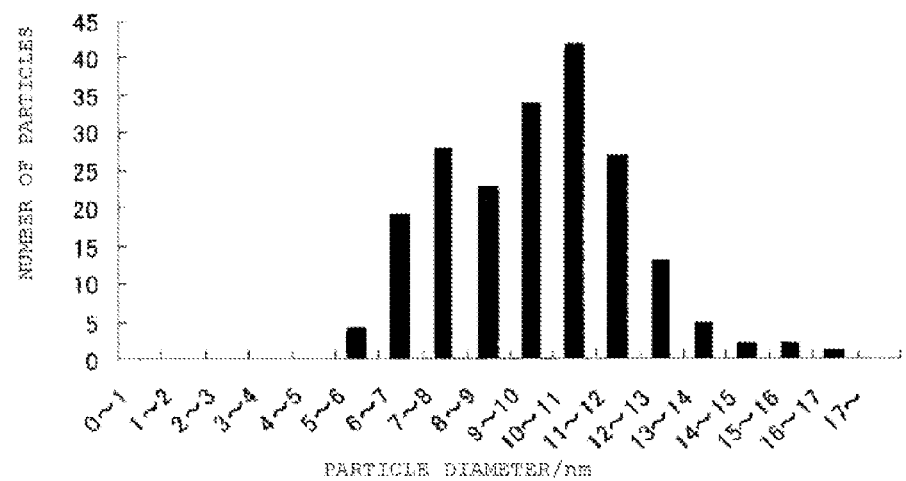
FIG. 18 shows the particle size distribution of the powder obtained in Example 5.
Figure 19:
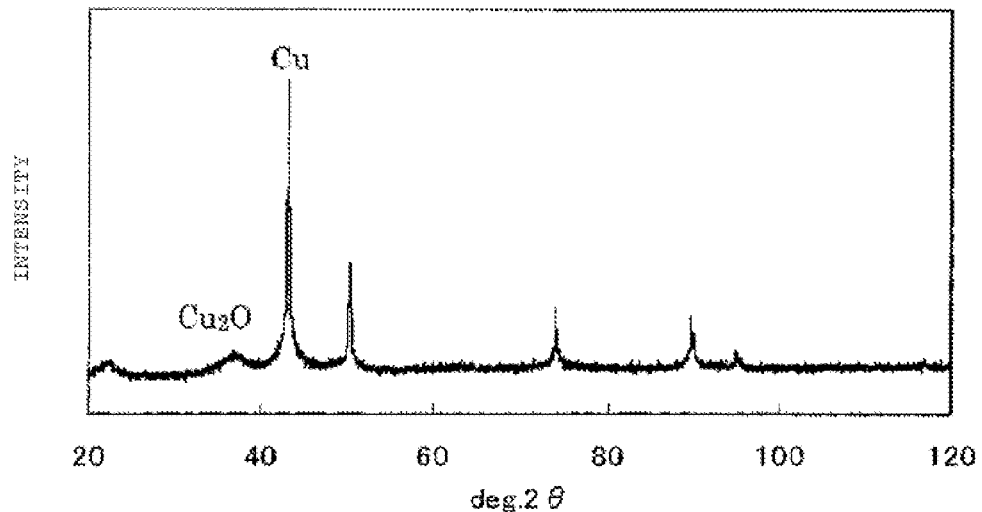
FIG. 19 shows the results of X-ray diffraction analysis (XRD) of the powder obtained in Example 5.

A powder (yield 0.31 g/89%, metal content 93%, mean particle diameter 9.7±2.1 nm) as obtained by a reaction similar to that of Example 4 except that the reaction conditions of Example 4 were changed from 160° C., 16 hours to 180° C., 4 hours. FIG. 16 shows the results for thermogravimetric (TG), change according to TG/DTA measurement, FIG. 17 shows a TEM image, FIG. 18 shows the particle size distribution, and FIG. 19 shows the results of X-ray diffraction analysis (XRD) of the resulting powder.

Example 6

Synthesis of CuNP/(C$_4$)$_3$N 3-ODO-1,2-PDO

Figure 20:
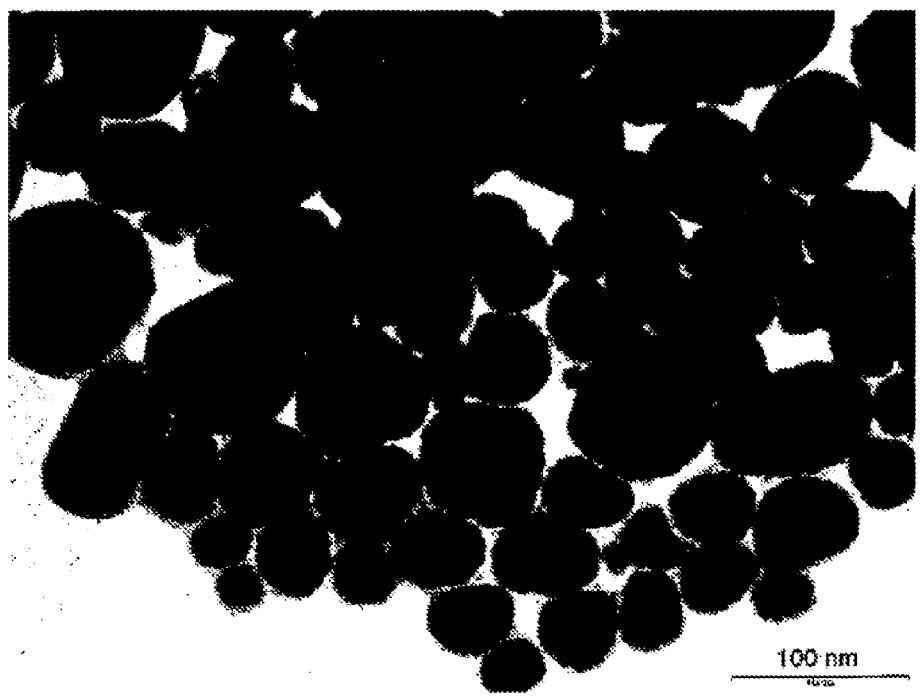
FIG. 20 shows a TEM image of the powder obtained in Example 6.
Figure 21:
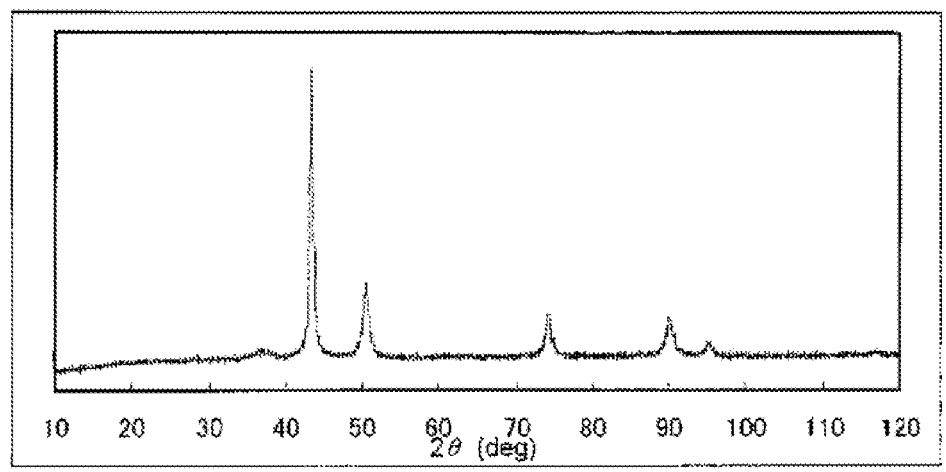
FIG. 21 shows the results of X-ray diffraction analysis (XRD) of the powder obtained in Example 6.

A powder (yield 0.34 g/100%, metal content 98%, particle size 50 to 100 nm) was obtained by a reaction similar to that of Example 1 except that (C$_4$)$_3$N was substituted for the amine (C$_8$)$_3$N and 3-ODO-1,2-PDO was substituted for the 1,2-DDO used in Example 1. FIG. 20 shows a TEM image and FIG. 21 shows the results of X-ray diffraction analysis (XRD) of the resulting powder.

Example 7

Synthesis of CuNP/(C$_8$)$_3$N 3-ODO-1,2-PDO

Figure 22:
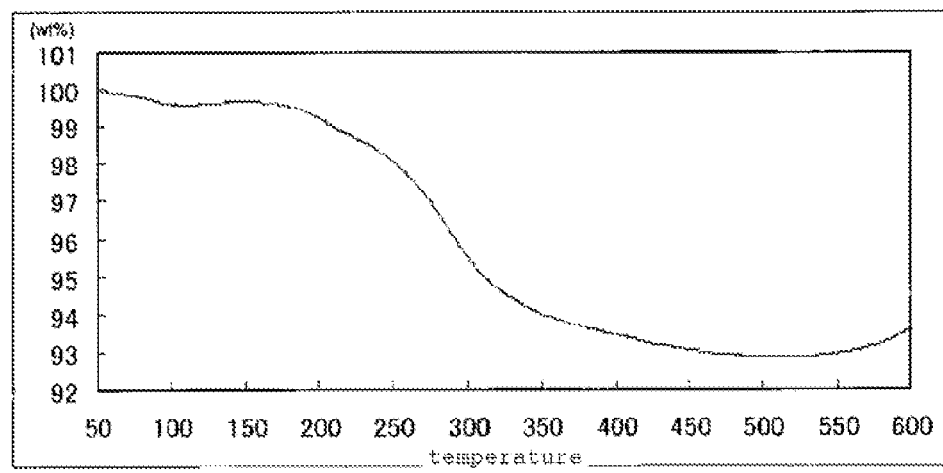
FIG. 22 shows the results for thermogravimetric (TG) change in TG/DTA measurement of the powder obtained in Example 7.
Figure 23:
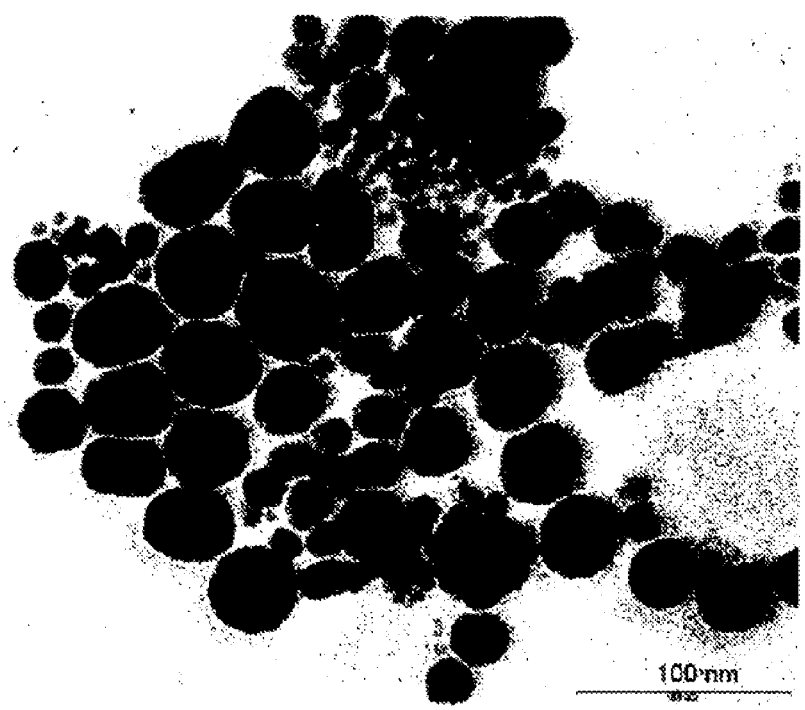
FIG. 23 shows a TEM image of the powder obtained in Example 7.
Figure 24:
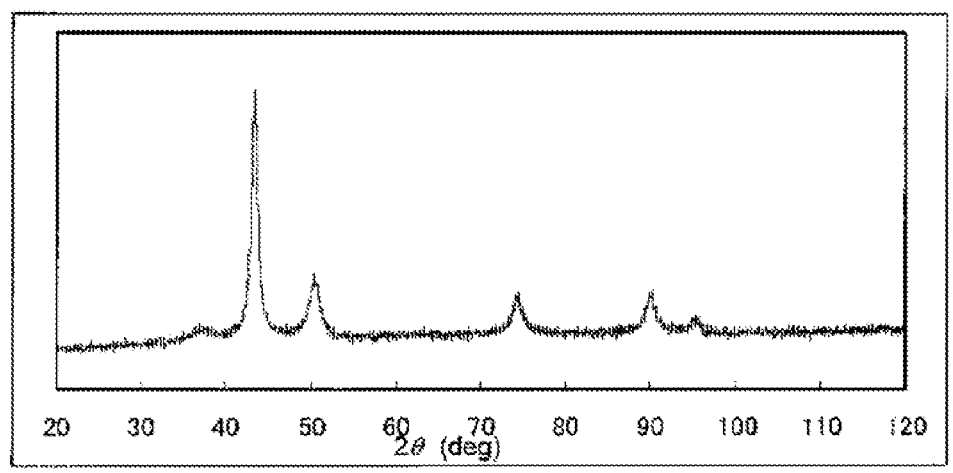
FIG. 24 shows the results of X-ray diffraction analysis (XRD) of the powder obtained in Example 7.

A powder (yield 0.36 g/100%, metal content 93%, particle size 10 to 50 nm) was obtained by a reaction similar to that of Example 1 except that 3-ODO-1,2-PDO was substituted or the 1,2-DDO used in Example 1. FIG. 22 shows the results for thermogravimetric (TG) change according to TG/DTA measurement, FIG. 23 shows a TEM image and FIG. 24 shows the results of X-ray diffraction analysis (XRD) of the resulting powder.

Example 8

Synthesis of CuNP/(2-EtC$_6$)$_3$N DDT

Figure 25:
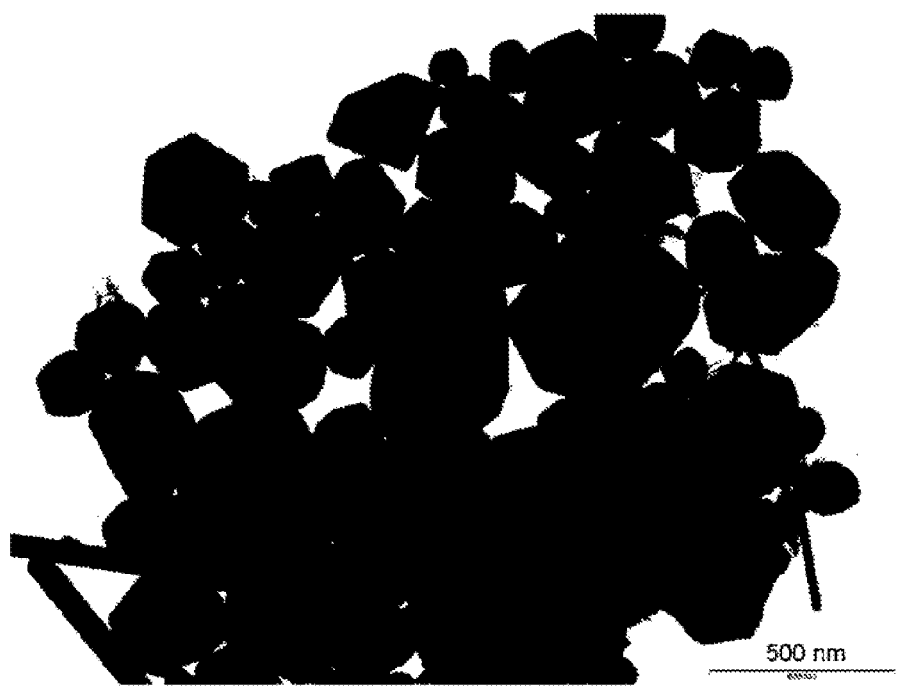
FIG. 25 shows a TEM image of the powder obtained in Example 8.
Figure 26:
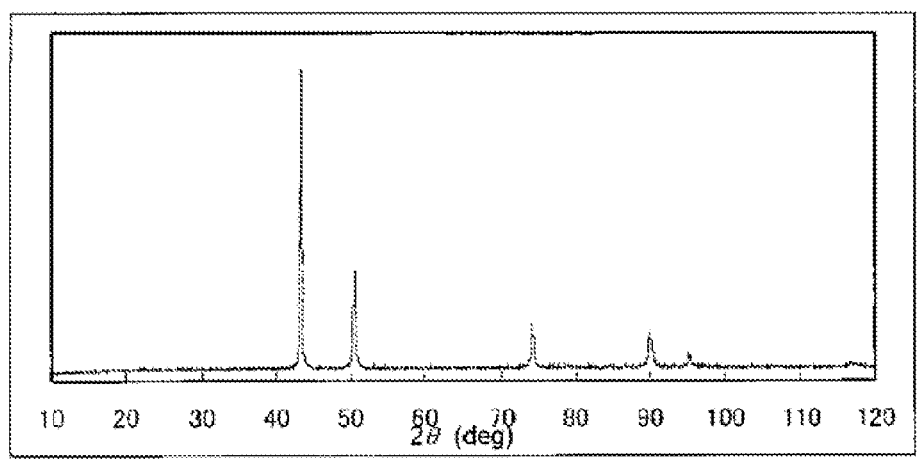
FIG. 26 shows the results of X-ray diffraction analysis (XRD) of the powder obtained in Example 8.

A powder (yield 0.29 g/91%, metal content 100%, particle size 100 to 500 nm) was obtained by a reaction similar to that of Example 4 except that DDT was substituted for the 1,2-DDO used in Example 4. FIG. 25 shows a TEM image, and FIG. 26 shows the results of X-ray diffraction analysis (XRD) of the resulting powder.

Comparative Example 1

Synthesis of CuNP/(2-EtC$_6$)$_3$N 1-C$_{12}$OH

Figure 27:
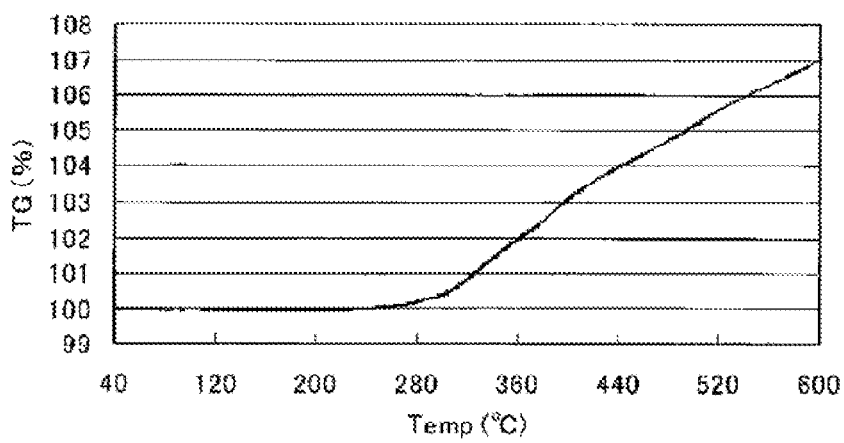
FIG. 27 shows the results for thermogravimetric (TG) chance in TG/DTA measurement of the powder obtained in Comparative Example 1.
Figure 28:
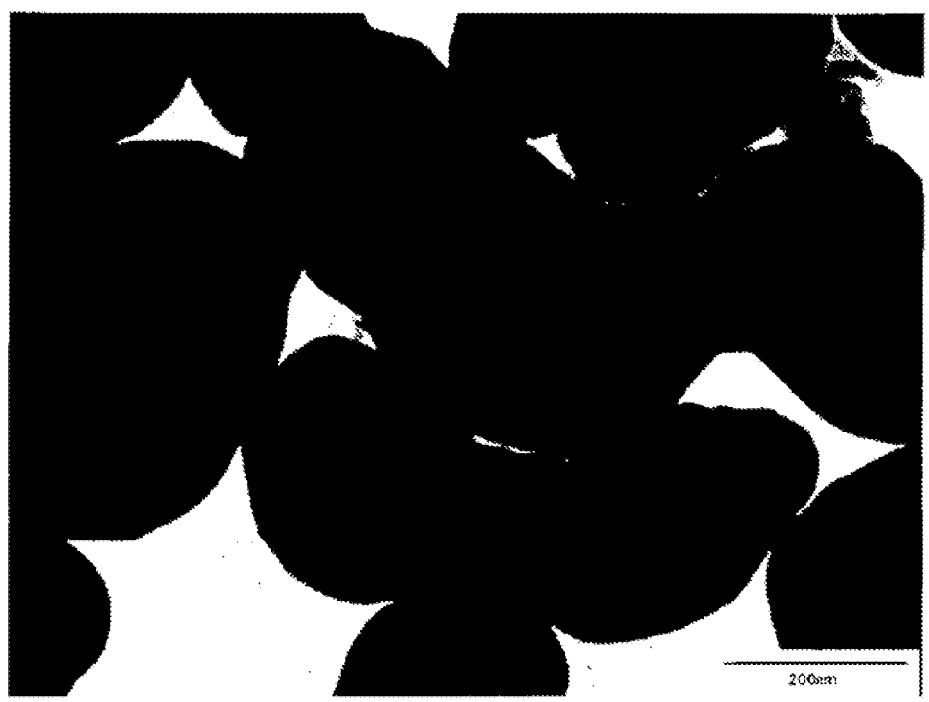
FIG. 28 shows a TEM image of the powder obtained in Comparative Example 1.
Figure 29:
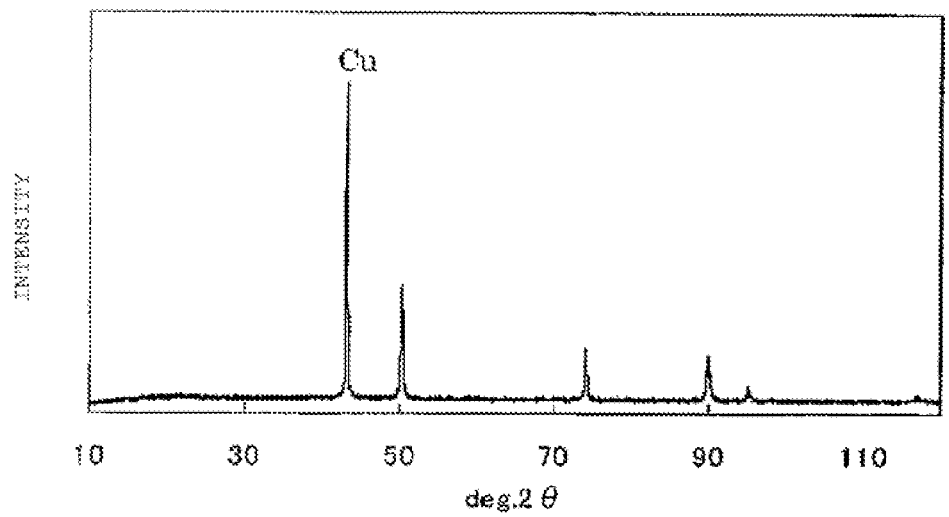
FIG. 29 shows the results of X-ray diffraction analysis (XRD) of the powder obtained in Comparative Example 1.

A powder (yield 0.24 g/74%, metal content 100%, bulky) was obtained by a reaction similar to that of Example 4 except that 1-C$_{12}$OH was substituted for the diol 1,2-DDO used in Example 4. FIG. 27 shows the results for thermogravimetric (TG) change according to TG/DTA measurement of the resulting powder. The bulky copper particles were oxidized by trace oxygen in the nitrogen atmosphere, resulting in increased weight. FIG. 2 shows a TEM image, and FIG. 29 shows the results of X-ray diffraction analysis (XRD).

Test Example 1

Figure 30:
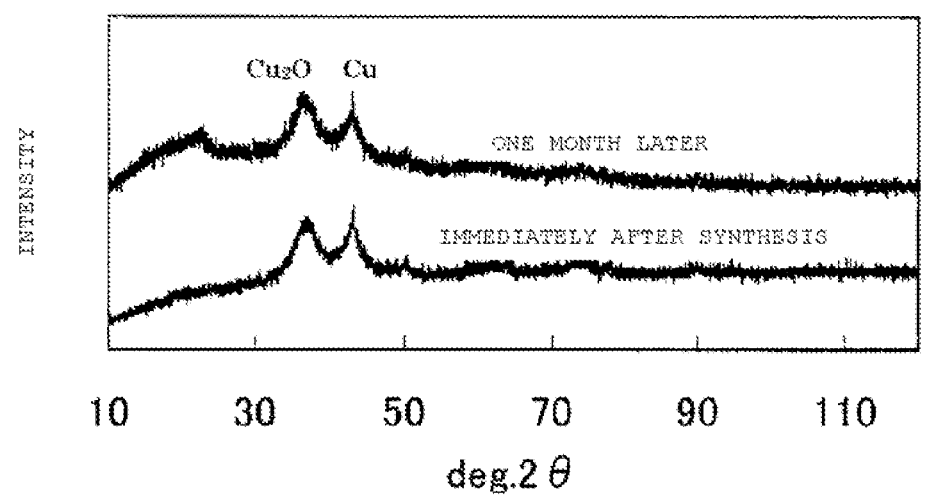
FIG. 30 shows the results of X-ray diffraction analysis (XRD) of CuNP/($C_8$)$_3$N 1,2-DDO immediately after synthesis and the same compound 1 month later.
Figure 31:
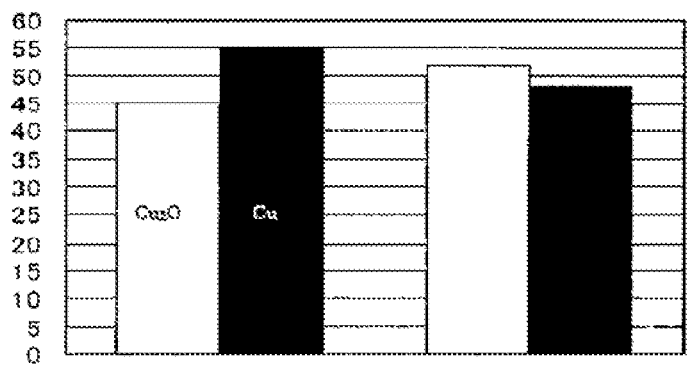
FIG. 31 shows changes over time in the intensity ratio in the XRD pattern of CuNP/($C_8$)$_3$N 1,2-DDO, the light-colored bars indicating $Cu_2O$, and the dark-colored bars indicating Cu.
Figure 32:
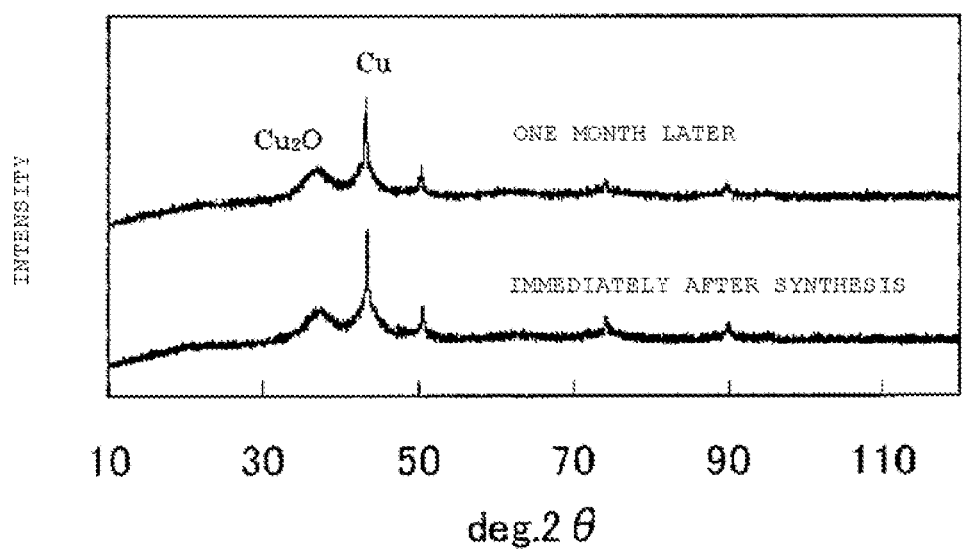
FIG. 32 shows the results of X-ray diffraction analysis (XRD) of CuNP/(iPr)$_2$NEt 1,2-DDO immediately after synthesis and the same compound 1 month later.
Figure 33:
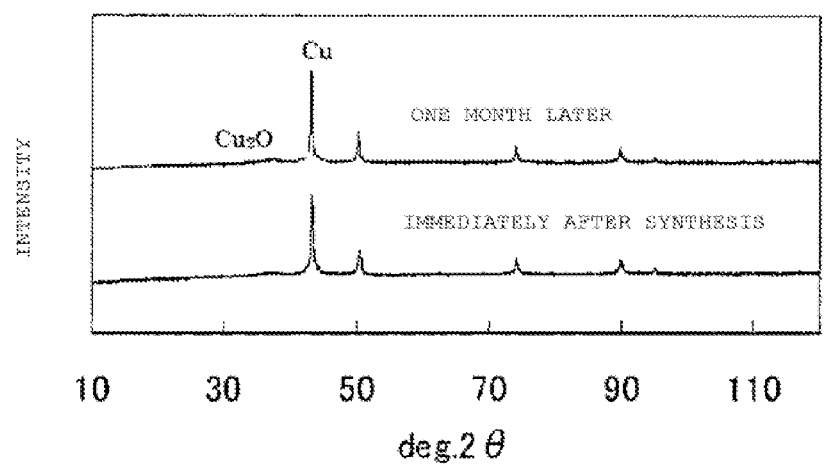
FIG. 33 shows the results of X-ray diffraction analysis (XRD) of CuNP/(2-Et$C_6$)$_3$N 1,2-DDO immediately after synthesis and the same compound 1 month later.
Figure 34:
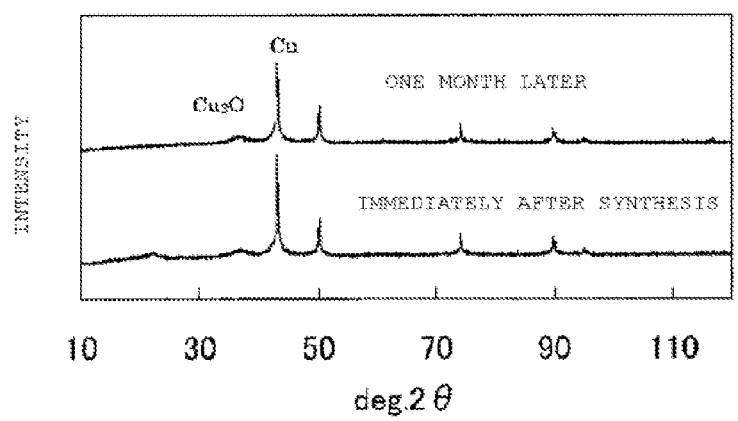
FIG. 34 shows the results of X-ray diffraction analysis (XRD) of CuNP/(2-Et$C_6$)$_3$N 1,2-DDO immediately after rapid synthesis and the same compound 1 month later.
Figure 35:
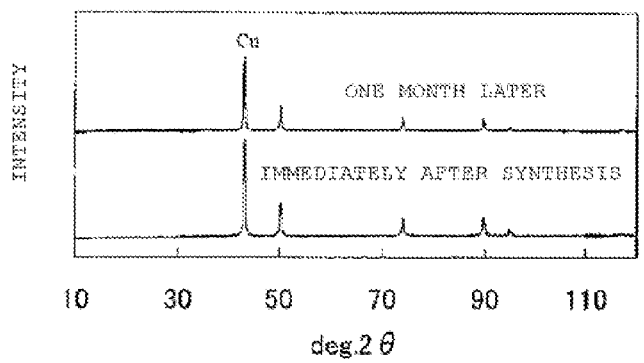
FIG. 35 shows the results of X-ray diffraction analysis (XRD) of CuNP/1,2-DDO immediately after synthesis and the same compound 1 month later.
Figure 36:
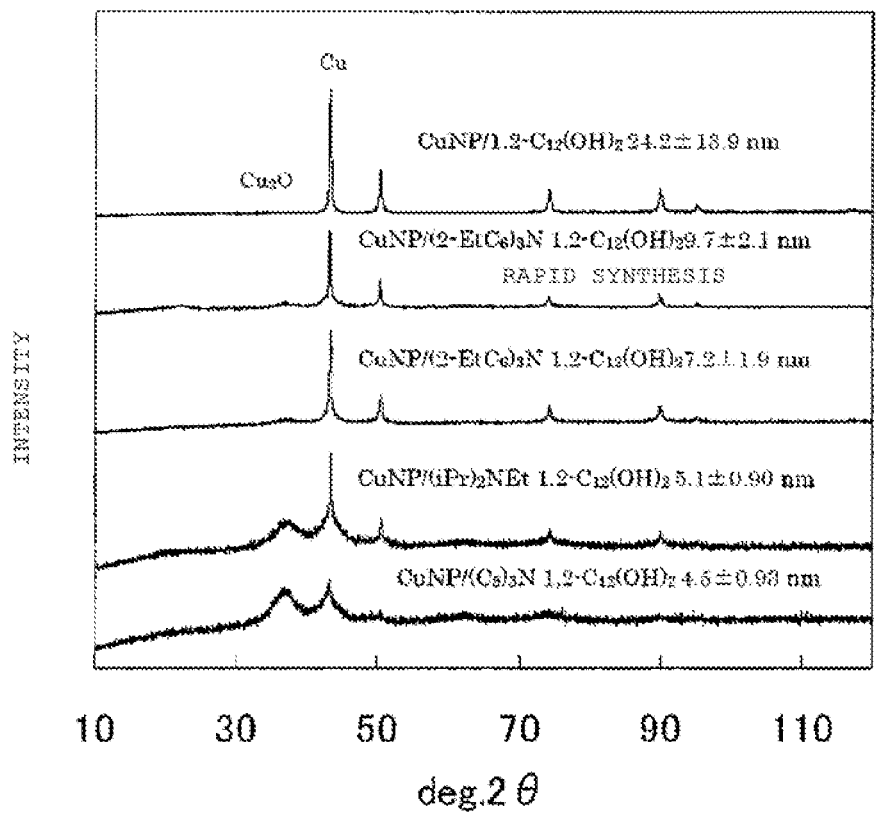
FIG. 36 shows a comparison of XRD patterns according to mean particle diameter.
Figure 37:
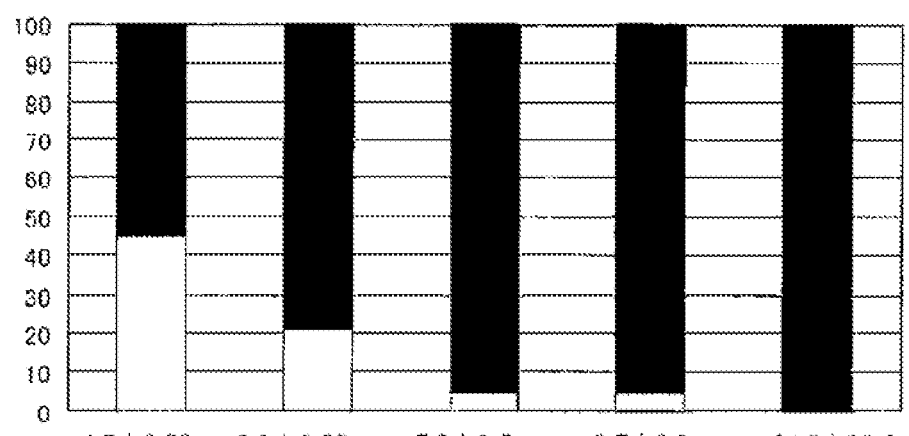
FIG. 37 shows the intensity ratio of Cu and $Cu_2O$ in the XRD pattern according to mean particle diameter, the light-colored bars indicating $Cu_2O$, and the dark-colored bars indicating Cu.

The oxidation resistance of the copper-containing nanoparticles obtained in the examples was investigated. In general, copper is known as an easily oxidized metal that is even more easily oxidized when made into nanoparticles. Of the synthesized nanoparticles, the powder X-ray diffraction (XRD) of those nanoparticles that were 100 nm or less in size and did not undergo fusion was compared immediately after synthesis and 1 month later to investigate oxidation resistance. The results are shown in FIGS. 30 and 31. In the case of the CuNP/(C$_8$)$_3$N 1,2-DDO, which had the smallest mean particle diameter (4.5±0.93 nm), a small increase in the diffraction pattern attributable to cuprous oxide was observed in powder X-ray diffraction analysis (XRD) 1 month later as compared to immediately after synthesis, confirming the occurrence of oxidation. When the oxidation resistance of CuNP/(iPr)$_2$NEt 1,2-DDO (mean particle diameter 5.1±0.90 nm), which has a larger mean particle diameter than CuNP/, (C$_8$)$_3$N 1,2-DDO, was measured in the same way, there was no oxidation as shown in FIG. 32. The oxidation resistance of CuNP/(2-Et-C$_6$)$_3$N 1,2-DDO (mean particle diameter 7.2±1.9 nm, FIG. 33), rapid synthesis CuNP/(2-EtC$_6$)$_3$N 1,2-DDO (mean particle diameter 9.65±2.07 nm, FIG. 34), and CuNP/1,2-DDO (mean particle diameter 24.15±3.94 nm, FIG. 35), which had even larger particle sizes, was also measured in the same way. The diffraction patterns in powder X-ray diffraction analysis (XRD) were roughly the same immediately after synthesis and 1 month later, and no chance of 1% or more was seen in the XRD patterns of Cu and Cu$_2$O. Comparing the powder X-ray diffraction (XRD) immediately after synthesis, it was confirmed that the diffraction pattern attributable to cuprous oxide shrinks as the mean particle diameter increases (FIGS. 36 and 37).

Test Example 2

Properties of Baked Film of Cu Nanoparticle Paste

A polyester dispersant and terpineol as a solvent were added to the CuNP/($C_8$)$_3$N 1,2-DDO copper nanoparticles synthesized in Example 1, and a few drops of toluene were dripped in to promote dispersibility. This was mixed until the toluene vaporized with no residue, to prepare a paste with a metal content of 60 wt %.

Figure 38:
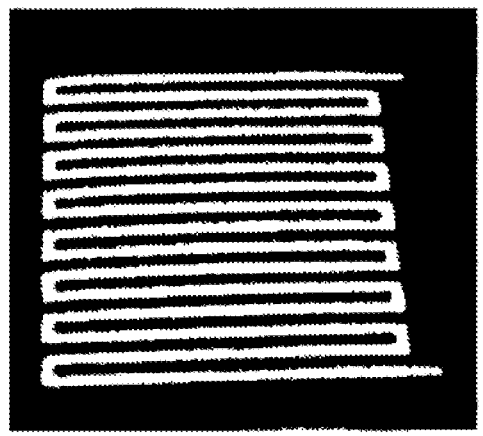
FIG. 38 shows a wiring pattern of formed on polyimide film in Test Example 2.

An electrode pattern was printed by screen printing using this paste, baked for 30 minutes at 350° C. atmosphere, and baked again for 30 minutes at 350° C. in a reducing atmosphere comprising 3 vol % hydrogen in nitrogen. The electrical properties of the resulting baked films are shown in Table 1. The specific resistance values of the baked films are 20 μΩcm or less, comparable to that of the bulk. FIG. 38 shows a wiring pattern formed on a polyimide film. Thus, a paste using the Cu-based nanoparticles of the present invention can be used favorably for wiring formation.

TABLE 1

| Entry | Baking conditions Air | Baking conditions $N_2$ + 3% $H_2$ | Specific resistance μΩcm |
|---|---|---|---|
| 1 | 350° C., 30 min | 350° C., 30 min | 15.1 |
| 2 | | | 18.5 |
| 3 | | | 7.4 |

Test Example 3

Bonding Test Using Cu Nanoparticles Paste

A polyester dispersant and terpineol as a solvent were added to the CuNP/($C_8$)$_3$N 1,2-DDO copper nanoparticles prepared in Example 1, and a few drops of toluene were dripped in to promote dispersibility. This was mixed until the toluene vaporized with no residue, to prepare a paste with a metal content of 60 wt %.

Figure 39:
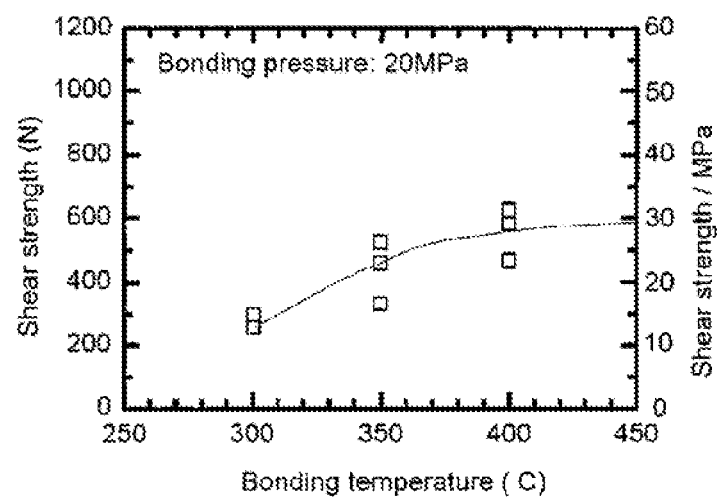
FIG. 39 shows shearing test results from the bonding experiment in Test Example 3.

A bonding test of oxygen-free copper was performed using this paste. Using ring-shaped oxygen-free copper 2 mm and 5 mm in diameter as the object of bonding, the paste was applied to the surface of the center of the 5 mm oxygen-free copper ring, and the 2 mm oxygen-free copper ring was inserted over the paste. This was heated to 150° C. and maintained for 300 seconds to dry the paste. 20 MPa of pressure was then applied, and the temperature was raised to a specific temperature (300 to 400° C.) and maintained for 300 seconds. This was then left to cool without pressure. FIG. 39 shows the results of a shearing test of the boded joint. These tests show that copper-containing nanoparticles paste of the present invention has a strength of 10 MPa or more, and is a suitable material for bonding applications.

The invention claimed is:

1. A method for manufacturing copper-containing nanoparticles, comprising a step of obtaining nanoparticles containing an organic component, copper and cuprous oxide by heat treating an organic copper compound at a temperature equal to or higher than a decomposition initiation temperature of the compound and lower than a complete decomposition temperature of the compound in a non-oxidative atmosphere in the presence of an organic material containing (1) a tertiary amine compound and (2) a 1,2-alkanediol and/or a derivative thereof, wherein the number of carbon atoms in the 1,2-alkanediol or a derivative thereof is 8 to 30.

2. The manufacturing method according to claim 1, wherein the organic copper compound is a copper salt of an organic acid having 5 or more carbon atoms.

3. The manufacturing method according to claim 1, wherein heat treatment is performed under conditions with no primary amine or secondary amine present.

4. Copper-containing, nanoparticles comprising an organic component, Cu and $Cu_2O$ in each particle, wherein an intensity ratio of $Cu_2O$ in an X-ray diffraction pattern is 50% or less given 100% as the total of intensities of Cu and $Cu_2O$, and wherein the organic component contains at least one of a 1,2-alkanediol with 5 or more carbon atoms, a derivative thereof and a component derived from these.

5. The copper-containing nanoparticles according to claim 4, wherein the content of the organic component is 25 wt % or less.

6. The copper-containing nanoparticles according to claim 4, wherein the change in the intensities of the Cu and $Cu_2O$ in the X-ray diffraction pattern immediately after oxidation resistance testing in which the copper-containing nanoparticles immediately after synthesis is left for 1 month at a temperature of 25° C. and a humidity of 60% in air is no more than 3% of intensities of the Cu and $Cu_2O$ in the X-ray diffraction pattern of the copper-containing nanoparticles immediately after synthesis.

7. The copper-containing nanoparticles according to claim 4, which is obtained by the manufacturing method according to claim 1.

8. A paste comprising the copper-containing nanoparticles according to claim 4 and at least one of a solvent and a viscosity modifying resin.

* * * * *